(12) United States Patent
Gerhardt et al.

(10) Patent No.: US 6,962,077 B2
(45) Date of Patent: Nov. 8, 2005

(54) SYSTEM AND METHOD OF MEASURING CONVECTION INDUCED IMPEDANCE GRADIENTS TO DETERMINE LIQUID FLOW RATES

(75) Inventors: Geoff C. Gerhardt, Millbury, MA (US); Keith Fadgen, Hope Valley, RI (US)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 10/328,986

(22) Filed: Dec. 23, 2002

(65) Prior Publication Data

US 2004/0118201 A1 Jun. 24, 2004

(51) Int. Cl.[7] .................................................. G01F 1/68
(52) U.S. Cl. ..................................................... 73/204.13
(58) Field of Search ........................ 73/204.13, 204.11, 73/204.17, 204.23, 202.5, 204.14, 204.15, 204.16, 204.18, 204.19

(56) References Cited

U.S. PATENT DOCUMENTS 3,801,902 A * 4/1974 Horowitz .................... 324/663
5,936,156 A * 8/1999 Roberts et al. ........... 73/204.19
6,085,588 A * 7/2000 Khadkikar et al. ....... 73/204.27
6,474,155 B1 * 11/2002 Berkcan et al. .......... 73/204.23

* cited by examiner

Primary Examiner—Edward Lefkowitz
Assistant Examiner—Corey D. Mack
(74) Attorney, Agent, or Firm—Lahive & Cockfield, LLP; Elizabeth A. Hanley

(57) ABSTRACT

A method and system for measuring the flow rate of a liquid or gas within a flow channel utilizing a centrally located excitation source and a plurality of sensor means. Said excitation means is comprised of a heating element coupled with an alternating current generator. Of the plurality of sensor means, at least one of said sensors is located in a position upstream of the excitation source location, and additionally a second of said plurality of sensors is located in a position downstream of the excitation source. Instantaneous fluid flow rate is calculated utilizing a high gain differential amplifier electrically coupled to said sensors, wherein the convectively induced inductive gradient of the flowing fluid is compared to the symmetrical zero flow induction gradient. Following such a comparison, a voltage signal proportional to the flow of fluid within the channel is derived.

20 Claims, 2 Drawing Sheets

SYSTEM AND METHOD OF MEASURING CONVECTION INDUCED IMPEDANCE GRADIENTS TO DETERMINE LIQUID FLOW RATES

TECHNICAL FIELD

The present invention relates generally to the measurement of liquid flow rates through a defined tube or channel, and specifically relates to the continuous flow measurement of flows less than 50 μL/min.

BACKGROUND OF THE INVENTION

There exist many examples of flow measurement through a fixed channel or tube. The simplest of these techniques utilizes a time of flight measurement, thereby only measuring flow through a channel for a fixed time period. Such sampling, therefore, results in finite flow measurements, incapable of accounting for dynamic variations in fluid flow during those periods outside of the time of flight measurement period.

More advanced techniques utilize an external excitation and measurement means. In exciting a fluid, a heating means is typically utilized, wherein such a heater is capable of delivering thermal energy to a closed fluid passageway. Two or more thermocouple probes, located upstream and downstream of the heating source, are then use to measure the local temperature differences at fixed points along the flow channel. Utilizing these components, a temperature gradient for a stagnant and flowing fluid can be obtained. Based upon this data, a finalized fluid flow may be calculated.

While the localized heating and temperature measurement of a fluid, as set forth above, is useful in a variety of industrial applications, the overall flow measurement accuracy is limited by several system inherent sources of error. Firstly, under the aforementioned flow measurement technique, system accuracy is directly related to thermocouple accuracy. To accurately determine fluid flow, each thermocouple must be able to discriminate between discrete differences in fluid temperatures at the associated thermocouple position. In systems in which there exists a large heat introduction in a quickly moving fluid, such temperature differences are greatly apparent. In light of this, determining fluid flow to the required degree of accuracy is made simple. In a setting in which there exists a small fluid flow velocity, the upstream and downstream temperature variations are greatly reduced. One such setting may be seen in a High Performance Capillary Liquid Chromatographic (HPLC) setting, in which fluid flows of less than 1 μL/min are not uncommon. In light of such a decrease in temperature variation, it becomes important to measure temperature to a much higher degree of accuracy. Such an increase in accuracy requires the use of a significantly more expensive thermocouple device.

Furthermore, under a temperature based system, there exist additional sources of system error which are not easily prevented. One such source of error lies in the thermal conduction of heat through the walls of the fluid channel. Such conductive heat transfer from heat source to thermocouple position results in the loss of flow measurement accuracy, as the thermocouple is no longer solely recording fluid temperature, but rather is under the influence of additional heat addition through the walls of the flow channel. Convective losses of heat along the flow channel exterior additionally contribute to the inherent system inaccuracies. Should a user elect to use externally mounted thermocouples, which are seated along the external surface of the flow channel, additional error is introduced as said external thermocouples are merely recording the fluid boundary layer temperature, as opposed to the interior fluid temperature at points away from the boundary layer. Numerous attempts have been made in the art to prevent these conductive and convective losses, all of which result in increases in system cost and complexity.

In light of the above, when operating in a low flow environment utilizing thermocouples as sensor means, the use of an internal thermocouple element is important in providing the greatest degree of flow rate measurement accuracy. Such internal thermocouples are in direct physical contact with the flowing fluid and offer great sensitivity and time response. Direct contact between an internal temperature probe and fluid, however, results in potential contamination of the fluid or of the temperature probe element. As the fluid is in direct contact with the internal probe, particulate matter suspended in a flowing fluid may contaminate the external temperature sensing region of a temperature probe, thereby resulting in inaccurate measurements. Furthermore, in the presence of highly corrosive or chemically reactive fluids, contact between the internal temperature probe and these fluids may result in the break down of the internal temperature probe surface, thereby resulting in the introduction of contaminant into the flowing fluid.

Additionally, the use of direct contact thermocouples require the introduction of numerous fittings, couplings and related alterations to the flow channel to adequately introduce the temperature measuring probes to the fluid flow. These extraneous additions introduce numerous sources of failure or leakage. In a high pressure operating environment, such as a HPLC setting, the addition of flanged or threaded couplings to a fluid channel requires skilled assembly of precision components. Such fittings introduce several potential failure locales when compared to a continuous, uninterrupted flow channel. Additionally, the introduction of these aforementioned temperature sensors into the fluid channel greatly increases system costs and complexity.

Finally, in a liquid chromatography environment, the addition of these aforementioned couplings, fittings and invasive temperature elements to the fluid pathway greatly increase the "dead volume" of the chromatographic column. The term "dead volume" is used to describe the unknown volume which is trapped in these various fittings, couplings, and thermocouple regions of the flow channel. This fluid may be either stagnant or dynamic in nature and may unpredictable escape into the fluid channel thereby causing the shape of the fluid pulse to be altered from the desired shape.

SUMMARY OF THE INVENTION

The present invention allows the user to measure fluid flow rate while simultaneously minimizing dead volume in a chromatographic environment wherein small fluid flows are present. The minimizing of dead volume reduces the cycle time of gradients, guards against convective and eddy current mixing, and aids in providing highly reproducible results. In attaining the foregoing and other objects, the present invention provides methods and apparatus for mounting an excitation source, as well as a plurality of sensor elements, to the external surface of a flow channel. The excitation source is located either in direct contact or in close proximity to the external surface of an existing flow channel. The excitation source is designed such that it may be mounted to a prexisting flow channel, thereby allowing retrofitting of existing systems. The excitation source may take the form of an alternating current (AC) generator coupled with an integral heating means. Additionally, alternate forms of excitations sources may be substituted as understood by those skilled in the art.

In addition to the excitation source, a plurality of sensor elements are located in positions upstream and downstream of the excitation source. Similar to the excitation source, these sensor elements are designed such that they may be installed on a prexisting flow channel without intrusive modifications. In light of this, dead volume within a flow channel is not increased by adding unnecessary couplings, fittings or other forms of extraneous paraphernalia associated with the installation of a direct contact sensor element. This excitation source comprises a heating element, used in elevating the temperature of the fluid, as well as an alternating current (AC) signal generator. This heater and AC generator are packaged together, and are located around the external surface of a flow channel. Following the addition of heat to the fluid, the fluid impedance will change. This change in impedance may be detected by a plurality of sensor means located in positions both upstream and downstream of the excitation source location. A preliminary impedance reading at upstream and downstream sensor locations under a zero flow condition may be recorded thereby providing a baseline representation of impedance conditions within the flow channel. Such a baseline representation will result in a symmetrical impedance gradient centered at the point of excitation. Furthermore, additional impedance readings from the aforementioned plurality of sensor means may be recorded under fluid flow conditions, thereby yielding a asymmetrical impedance gradient around the central excitation element. These aforementioned sensor means are in electrical communication with a calculation means, wherein said calculation means comprises a high gain differential amplifier capable of receiving electrical information from said sensors. This high gain differential amplifier yields an electrical voltage proportional to the fluid flow rate within the flow channel. Under a zero flow condition, for example, this calculation means will yield a zero output voltage. Under a flowing fluid scenario, for example, the output of this high gain differencing amplifier may be represented by a positive voltage proportional to the fluid velocity within the channel. The flow rate measurement may be continuous in nature and provides instantaneous values of flow rate within a flow channel. In light of such an arrangement, continuous flow measurement may be calculated which represent actual flow conditions within a channel at any instant in time. When coupled to a High Pressure Liquid Chromatographic system (HPLC), the present invention may be utilized in providing flow feedback information to the HPLC system operating in a sub 50 $\mu$L/min environment, to thereby verify delivery performance of the pumping means.

DETAILED DESCRIPTION OF THE INVENTION

Figure 1:
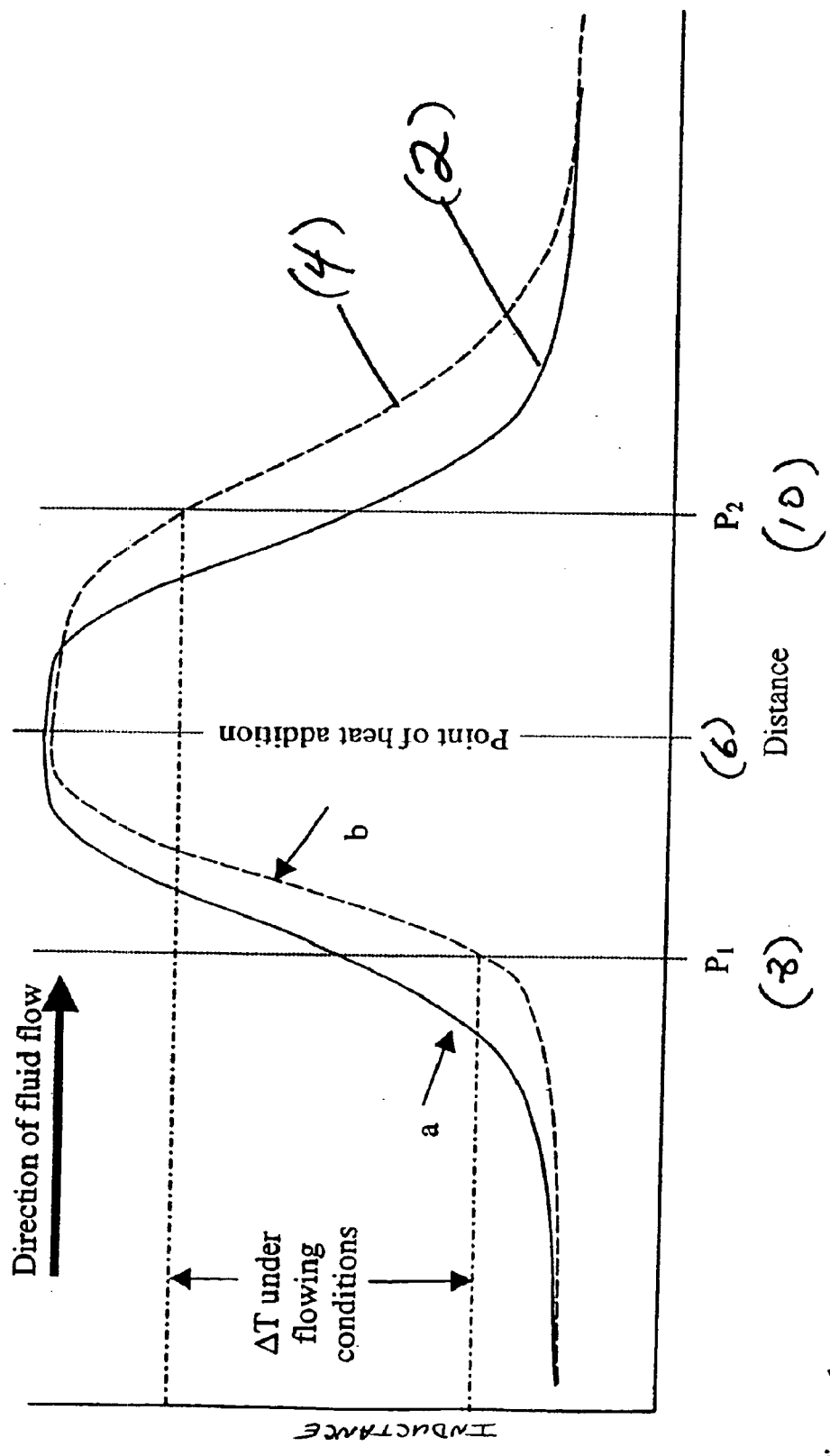
FIG. 1 is a graph depicting the typical induction gradient for a stagnant and flowing fluid contained within a flow channel following the addition of heat at a fixed point.
Figure 2:
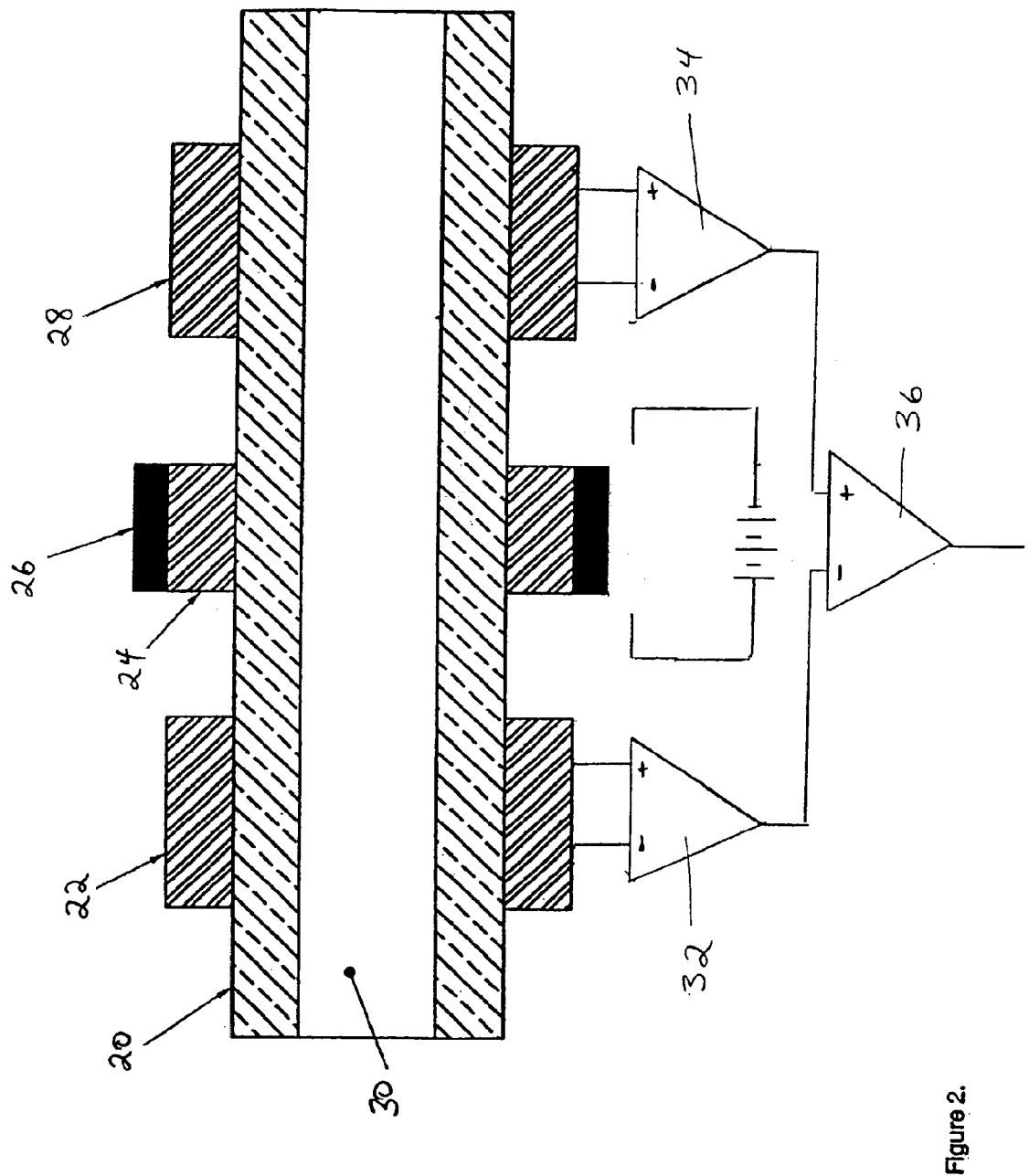
FIG. 2 is a schematic of an embodiment of the present invention, in which contactless conductive pickups are employed in positions upstream and downstream of an excitation source. Such contactless conductive pickups are capable of measuring fluid impedance, and are in electrical communication with a high gain differential amplifier.

FIGS. 1 and 2, wherein like parts are designated by like reference numerals throughout, illustrate an example embodiment of a system and method suitable for measuring the flow of a liquid through a flow channel. This system and method may be used alone or in combination with a High Pressure Liquid Chromatography device. Although the present invention is described with reference to the example embodiments illustrated in the figures, it should be understood that many alternative forms could embody the present invention. One of ordinary skill in the art will additionally appreciate different ways to alter the parameters of the embodiments disclosed, such as the heating means, size, or type of sensor means, in a manner still in keeping with the spirit and scope of the present invention.

Referring to FIG. 1, a static impedance distribution (2) is shown wherein thermal energy and an alternating current signal is introduced at a fixed excitation point (6), and fluid impedance is measured at fixed distances upstream (8) and downstream (10) of the point of thermal energy introduction (6). Additionally, an impedance/distance distribution in a flowing fluid environment (4) is depicted wherein the excitation point (6) remains the same and inductance is measured at the same fixed upstream position (8) and downstream position (10).

Referring to FIG. 2 of the present application, a flow channel (20) is depicted which utilizes an excitation source comprising a heater element (26) and an alternating current signal generator (24). Said elements are in contact with the external wall of the flow channel, and thereby introduce energy to the fluid (30) within the flow channel (20). These excitation elements are not in direct physical contact with the fluid (30) contained within the flow channel (12) thereby preventing contamination of the fluid or the heating element (26) or the alternating current signal generator (24). Additionally, a first contactless conductive impedance sensor (22), located at a point upstream of the AC signal generator (24) and heat source (26) is taught. A second contactless conductive impedance sensor (28) is located at a point downstream of the location of the excitation elements. This upstream sensor (22) and downstream sensor (28) are located at fixed distances from the heat source (26) and AC current generating source (24). The upstream and downstream sensors are individually amplified by high gain amplifiers (32) (34) and are processed by a high gain differencing amplifier (36) thereby yielding a flow dependent output voltage signal.

What is claimed is:

1. A flow rate measuring meter, comprising:
    a flow channel with an interior passage having an input end and an output end, wherein said input end is capable of receiving a liquid whose flow rate is to be measured;
    an external excitation source mounted to an external surface of an external wall of the flow channel for exciting the liquid;
    a plurality of sensor means for measuring a fluid impedance of liquid within the flow channel, wherein at least one of said sensor means is located upstream of the excitation source and a second sensor means is located in a position downstream of said excitation source, wherein said plurality of sensor means comprises conductive pickups that do not contact said liquid in said flow channel; and
    a calculation means in communication with said plurality of sensor means, wherein output of said calculation means is a flow rate dependent electrical signal.

2. The meter of claim 1, wherein said excitation source comprises a heating means coupled to an alternating current generating conductor.

3. The meter of claim 1, wherein said excitation source is in close proximity with the external wall of the flow channel.

4. The meter of claim 1, wherein said excitation source intimately contacts the external wall of the flow channel without compromising the physical integrity of said channel.

5. The meter of claim 1, wherein said excitation source may be located around the external wall of a pre-existing flow channel.

6. The plurality of sensor means of claim 1, wherein said sensor means intimately contact the external wall of the flow channel without compromising the physical integrity of the flow channel.

7. The plurality of sensor means of claim 1, wherein said sensor means may be located around the external wall of a pre-existing flow channel.

8. The meter of claim 1, wherein said sensor means are located such that they are external to the fluid contained within the interior passage of the flow channel, yet are in conductive contact with the external surface of the flow channel.

9. The calculation means of claim 1, wherein said calculation means comprises a high gain differencing amplifier in electrical communication with said plurality of sensor means such that the output of this high gain differencing amplifier is a voltage signal proportional to the flow rate within the flow channel.

10. A method for measuring flow rate comprising the steps of:
   introducing a flowing fluid to the internal passage of a flow channel;
   exciting the fluid utilizing at least one external excitation source mounted to an external surface of an external wall the flow channel;
   measuring an amount of additional energy added to the flowing fluid at a first position upstream of the excitation source and at a second position downstream of the excitation source by sensing fluid impedance, wherein the step of measuring an amount of additional energy comprises sensing fluid impedance utilizing a plurality of sensor means in conductive contact with the external surface of the flow channel; and
   calculating the instant flow rate of the flowing fluid based upon the asymmetrical fluid impedance gradient of the flowing fluid as determined by said step of measuring.

11. The method of claim 10, wherein the step of exciting the fluid comprises utilizing a thermal heating element and an alternating current generating conductor.

12. The method of claim 11, wherein the step of calculating the asymmetrical fluid impedance gradient further comprises the step recording fluid impedance under a flowing fluid condition.

13. The method of claim 10, further comprising the step of calculating said asymmetrical fluid impedance gradient by recording fluid impedance under a zero flow condition.

14. The method of claim 10, further comprising the step of calculating continuous fluid flow through a flow channel utilizing a high gain differencing amplifier to produce a voltage signal representative of instantaneous fluid flow conditions based on said step of measuring.

15. The method of claim 14, comprising the steps of comparing a representative voltage signal for zero flow conditions with that of the voltage signal under flowing fluid conditions, thereby yielding a voltage signal representative of instantaneous fluid flow.

16. A high performance liquid chromatography (HPLC) system, including a flow rate measuring meter, the improvement comprising:
   a flow channel;
   an external excitation source mounted to an external surface of said flow channel for exciting a liquid in the flow channel;
   a plurality of sensor means wherein at least one of said plurality is located in a position upstream of said excitation source and a second of said plurality is located in a position downstream of said excitation source, wherein said plurality of sensor means comprises impedance sensors that do not contact said liquid in said flow channel; and
   a calculation means in electrical communication with said plurality of sensor means for receiving signals from said plurality of sensor means indicative of a fluid impedance of a fluid within the flow channel, wherein the output of said calculation means is a voltage signal proportional to the instant flow rate of the fluid within the flow channel.

17. The high performance liquid chromatography system of claim 16, wherein said flow channel is designed to minimize dead volume.

18. The high performance liquid chromatography system of claim 16, wherein said flow measuring meter is used as an element within a flow sensing feedback means for verifying delivery of a fluid with a flow rate of less than 50 $\mu$L/min.

19. The high performance liquid chromatography system of claim 16, wherein said flow meter is capable of continuous flow measurements of a flowing fluid within a flow channel.

20. The high performance liquid chromatography system of claim 16, wherein said external excitation source comprises a heating element and an alternating current generating element.

* * * * *